(12) United States Patent
Ros et al.

(10) Patent No.: US 10,166,542 B2
(45) Date of Patent: Jan. 1, 2019

(54) METHODS, SYSTEMS AND APPARATUS FOR MICROFLUIDIC CRYSTALLIZATION BASED ON GRADIENT MIXING

(71) Applicants: Alexandra Ros, Phoenix, AZ (US); Bahige G. Abdallah, Casa Grande, AZ (US)

(72) Inventors: Alexandra Ros, Phoenix, AZ (US); Bahige G. Abdallah, Casa Grande, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 15/510,126

(22) PCT Filed: Sep. 17, 2015

(86) PCT No.: PCT/US2015/050616
§ 371 (c)(1),
(2) Date: Mar. 9, 2017

(87) PCT Pub. No.: WO2016/044545
PCT Pub. Date: Mar. 24, 2016

(65) Prior Publication Data
US 2017/0297024 A1    Oct. 19, 2017

Related U.S. Application Data

(60) Provisional application No. 62/051,642, filed on Sep. 17, 2014.

(51) Int. Cl.
| | | |
|---|---|---|
| *C30B 7/08* | (2006.01) | |
| *B01L 3/00* | (2006.01) | |
| *G01N 1/38* | (2006.01) | |

(52) U.S. Cl.
CPC ..... *B01L 3/502761* (2013.01); *B01L 3/50273* (2013.01); *B01L 3/502715* (2013.01);
(Continued)

(58) Field of Classification Search
CPC ................... C30B 7/08; C30B 7/00
See application file for complete search history.

(56) References Cited

U.S. PATENT DOCUMENTS

| | | |
|---|---|---|
| 6,822,180 B2 | 11/2004 | Fujii et al. |
| 7,584,857 B2 | 9/2009 | Boehm et al. |

(Continued)

FOREIGN PATENT DOCUMENTS

WO    2013/075081 A2    5/2013

OTHER PUBLICATIONS

Doak R.B. et al., "Microscopic linear liquid streams in vacuum: Injection of solvated biological samples into X-ray free electron lasers", AIP Conference Proceedings, vol. 1501, pp. 1314-1323 (2012).

(Continued)

*Primary Examiner* — Robert M Kunemund
(74) *Attorney, Agent, or Firm* — Michael Best & Friedrich LLP

(57) ABSTRACT

A microfluidic apparatus, systems and methods for microfluidic crystallization based on gradient mixing. In one embodiment, the apparatus includes (a) a first layer, (b) a plurality of first channels and a plurality of vacuum chambers both arranged in the first layer, where the plurality of vacuum chambers are each coupled to at least one of the first channels, (c) a membrane having first and second surfaces, where the first surface of the membrane is coupled to the first layer, (d) a second layer coupled to the second surface of the membrane, (e) a plurality of wells and a plurality of second channels both arranged in the second layer, where the wells (Continued)

are each coupled to at least one of the plurality of second channels and (f) a plurality of barrier walls each disposed in the plurality of second channels and arranged opposite to one of the plurality of vacuum chambers.

20 Claims, 8 Drawing Sheets

(52) U.S. Cl.
CPC .......... *B01L 3/502738* (2013.01); *G01N 1/38* (2013.01); *B01L 2200/0652* (2013.01); *B01L 2300/0654* (2013.01); *B01L 2300/0816* (2013.01); *B01L 2300/0848* (2013.01); *B01L 2300/0861* (2013.01); *B01L 2300/0864* (2013.01); *B01L 2300/0867* (2013.01); *B01L 2300/0887* (2013.01); *B01L 2300/0896* (2013.01); *B01L 2300/123* (2013.01); *B01L 2300/16* (2013.01); *B01L 2400/049* (2013.01); *B01L 2400/0424* (2013.01); *B01L 2400/0487* (2013.01); *B01L 2400/0655* (2013.01)

(56) References Cited

U.S. PATENT DOCUMENTS

| | | | |
|---|---|---|---|
| 8,272,576 | B2 | 9/2012 | Doak et al. |
| 8,827,548 | B2 * | 9/2014 | Roukes ................. G01L 1/044 374/31 |
| 9,192,944 | B2 | 11/2015 | Ros et al. |
| 2010/0224255 | A1 | 9/2010 | Mathies et al. |
| 2010/0303687 | A1 | 12/2010 | Blaga et al. |
| 2012/0021523 | A1 | 1/2012 | Fowler et al. |
| 2012/0266986 | A1 | 10/2012 | Wimberger-Friedl et al. |
| 2013/0032235 | A1 | 2/2013 | Johnston et al. |
| 2013/0313336 | A1 | 11/2013 | Doak et al. |
| 2014/0038279 | A1 * | 2/2014 | Ingber ................... C12M 25/02 435/297.2 |
| 2015/0087559 | A1 * | 3/2015 | Putnam .................. G01N 21/05 506/39 |

OTHER PUBLICATIONS

Zhu J. et al., Dielectrophoretic focusing of particles in a microchannel constriction using DC-biased AC flectric fields, Electrophoresis, vol. 30, Issue 15 pp. 2668-2675 (2009).
Pohl H.A. et al., "Dielectrophoretic Force", J. Theor. Biol., vol. 37, pp. 1-13 (1972).
Pohl H.A. et al., "Dielectrophoresis of Cells", Biophysical Journal, vol. 11, pp. 711-727 (1971).
International Search Report for PCT/US2015/050616, dated Jan. 18 2016.
Written opinion for PCT/US2015/050616, dated Jan. 18 2016.
Dertinger S.K.W. et al., "Generation of Gradients Having Complex Shapes Using Microfluidic Networks", Anal. Chem., 73, 1240-1246 (2001).
Jeon N.L. et al., "Generation of Solution and Surface Gradients Using Microfluidic Systems", Langmuir, 16, 8311-8316 (2000).
Lin. et al., "Parallel mixing of photolithographically defined nanoliter volume using elastomeric microvalve arrays", Electrophoresis, 26, 3758-3764 (2005).
The International Search Report (ISR) with Written Opinion for PCT/US2015/050616 dated Dec. 7, 2015, pp. 1-13.
Spence J.C. et al., "X-ray lasers for structural and dynamic Biology", Rep Prog Phys, vol. 75, Issue 10, pp. 102601 (2012).
Almen M.S. et al., "Mapping the human membrane proteome: a majority of the human membrane proteins can be classified according to function and evolutionary origin", BMC Biology, vol. 7, Issue 1, pp. 50 (2009).

Lundstrom K., "Structural genomics and drug discovery", Journal of Cellular and Molecular Medicine, vol. 11, Issue 2, pp. 224-238 (2007).
Schubert W.D. et al., "Photosystem I of Synechococcus elongatus at 4 A Resolution: Comprehensive Structure Analysis", Journal of Molecular Biology, vol. 272, Issue 5, pp. 741-769 (1997).
Fromme P. et al., "Femtosecond nanocrystallography using X-ray lasers for membrane protein structure determination", Current Opinion in Structural Biology, vol. 21, Issue 4, pp. 509-516 (2011).
Jordan P. et al., "Three-dimensional structure of cyanobacterial photosystem I at 2.5 Å resolution", Nature, vol. 411, Jun. 21, pp. 909-917 (2001).
Fromme P et al., "Improved isolation and crystallization of Photosystem I for structural analysis", Biochimica et Biophysica Acta, vol. 1365, Issue 1-2, pp. 175-184 (1998).
Hunter M.S. et al., "X-ray Diffraction from Membrane Protein Nanocrystals", Biophysical Journal, vol. 100, Issue 1, pp. 198-206 (2011).
Chapman H.N., "X-ray imaging beyond the limits", Nature Materials, vol. 8, Issue 4, pp. 299-301 (2009).
Redecke L. et al., "Natively Inhibited Trypanosoma brucei Cathepsin B Structure Determined by Using an X-ray Laser", Science, vol. 339, Issue 6116, pp. 227-230 (2013).
Chapman H. N. et al., "Femtosecond X-ray protein nanocrystallography", Nature-London, vol. 470, Issue 7332, pp. 73-77 (2011).
Boutet S. et al., "High-Resolution Protein Structure Determination by Serial Femtosecond Crystallography", Science, vol. 337, Issue 6092, pp. 362-364 (2012).
Hunter M.S. et al., "Toward structure determination using membrane-protein nanocrystals and microcrystals", Methods, vol. 55, Issue 4, pp. 387-404 (2011.
Srivastava S.K. et al., "DC insulator dielectrophoretic applications in microdevice technology: a review", Analytical and Bioanalytical Chemistry, vol. 399, Issue 1, pp. 301-321 (2011).
Majewski P. et al., "Synthesis, Surface Modifications, and Size-Sorting of Mixed Nickel-Zinc Ferrite Colloidal Magnetic Nanoparticles", Chemistry : a European journal, vol. 14, Issue 26, pp. 7961-7968 (2008).
Chen G. et al., "High-Purity Separation of Gold Nanoparticle Dimers and Trimers", Journal of the American Chemical Society, vol. 131, Issue 12, pp. 4218-4219 (2009).
Novak J. P. et al., "Purification of Molecularly Bridged Metal Nanoparticle Arrays by Centrifugation and Size Exclusion Chromatography", Analytical Chemistry, vol. 73, Issue 23, pp. 5758-5761 (2001).
Akthakul A. et al., "Size fractionation of metal nanoparticles by membrane filtration", Advanced Materials, vol. 17, Issue 5, pp. 532-535 (2005).
Gerion D. et al., "Sorting Fluorescent Nanocrystals with DNA", Journal of the American Chemical Society, vol. 124, Issue 24, pp. 7070-7074 (2002).
Yang J. et al., "Size sorting of Au and Pt nanoparticles from arbitrary particle size distributions", Analytica Chimica Acta, vol. 546, Issue 2, pp. 133-138 (2005).
Jores K. et al., "Investigations on the structure of solid lipid nanoparticles (SLN) and oil-loaded solid lipid nanoparticles by photon correlation spectroscopy, field-flow fractionation and transmission electron microscopy", Journal of Controlled Release, vol. 95, Issue 2, pp. 217-227 (2004).
Calzolai L. et al., "Separation and characterization of gold nanoparticle mixtures by flow-field-flow fractionation", Journal of Chromatography A, vol. 1218, Issue 27, pp. 4234-4239 (2011).
Pamme N. et al., "On-Chip Free-Flow Magnetophoresis: Continuous Flow Separation of Magnetic Particles and Agglomerates", Analytical Chemistry, vol. 76, Issue 24, pp. 7250-7256 (2004).
Pamme N. et al., "Continuous sorting of magnetic cells via on-chip free-flow magnetophoresis", Lab on A Chip, vol. 6, Issue 8, pp. 974-980 (2006).
Latham A.H. et al., "Capillary Magnetic Field Flow Fractionation and Analysis of Magnetic Nanoparticles", Analytical Chemistry, vol. 77, Issue 15, pp. 5055-5062 (2005).
Gascoyne P.R. et al., "Particle separation by dielectrophoresis", Electrophoresis, vol. 23, Issue 13, pp. 1973-1983 (2002).

(56) References Cited

OTHER PUBLICATIONS

Srivastava S.K. et al., "A continuous DC-insulator dielectrophoretic sorter of microparticles", Journal of chromatography. A, vol. 1218, Issue 13, pp. 1780-1789 (2011).
Srivastava S.K. et al., "Direct current insulator-based dielectrophoretic characterization of erythrocytes: ABO—Rh human blood typing", Electrophoresis, vol. 32, Issue 18, pp. 2530-2540 (2011).
Salomon S. et al., "A dielectrophoretic continuous flow sorterusing integrated microelectrodes coupled to a channel constriction", Electrophoresis, vol. 32, Issue 12, pp. 1508-1514 (2011).
Fiedler S. et al., "Dielectrophoretic Sorting of Particles and Cells in a Microsystem", Analytical Chemistry, vol. 70, Issue 9, pp. 1909-1915 (1998).
Muller T. et al., "A 3-D microelectrode system for handling and caging single cells and particles", Biosensors & Bioelectronics, vol. 14, Issue 3, pp. 247-256 (1999).
Cheng I.F. et al., "A continuous high-throughput bioparticle sorter based on 3D traveling-wave dielectrophoresis", Lab on a chip, vol. 9, Issue 22. pp. 3193-3201 (2009).
Holmes D. et al., "On-chip high-speed sorting of micron-sized particles for high-throughput analysis", IEE proceedings. Nanobiotechnology, vol. 152, Issue 4, pp. 129-135 (2005).
Kralj J.G. et al., "Continuous Dielectrophoretic Size-Based Particle Sorting", Analytical Chemistry, vol. 78, Issue 14, pp. 5019-5025 (2006).
Pommer M.S. et al., "Dielectrophoretic separation of platelets from diluted whole blood in microfluidic channels", Electrophoresis, vol. 29, Issue 6, pp. 1213-1218 (2008).
Bligh M. et al., "Sorting microparticles into lateral streams using a two-phase rectangular electrokinetic array", Journal of Micromechanics and Microengineering, vol. 18, Issue 4, pp. 045002 (2008).
Ozuna-Chacon S. et al., "Performance characterization of an insulator-based dielectrophoretic microdevice", Electrophoresis, vol. 29, Issue 15, pp. 3115-3222 (2008).
Hellmich W. et al., "Poly(oxyethylene) Based Surface Coatings for Poly(dimethylsiloxane) Microchannels", Langmuir, vol. 21, Issue 16, pp. 7551-7557 (2005).
Cummings E.B. et al., "Dielectrophoresis in Microchips Containing Arrays of Insulating Posts: Theoretical and Experimental Results", Analytical Chemistry, vol. 75, Issue 18, pp. 4724-4731 (2003).
Nakano A. et al., "Tuning direct current streaming dielectrophoresis of proteins", Biomicrofluidics, vol. 6, Issue 3, pp. 34108 (2012).
Nakano A. et al., "Immunoglobulin G and bovine serum albumin streaming dielectrophoresis in a microfluidic device", Electrophoresis, vol. 32, Issue 17, pp. 2314-2322 (2011).
Martinez-Duarte R. et al., "Microfabrication technologies in dielectrophoresis applications—A review", Electrophoresis, vol. 33, Issue 21, pp. 3110-3132 (2012).
Lapizco-Encinas B.H. et al., "Insulator-based dielectrophoresis for the selective concentration and separation of live bacteria in water", Electrophoresis, vol. 25, Issue 10-11, pp. 1695-1704 (2004).
Viefhues M. et al., "Physisorbed surface coatings for poly(dimethylsiloxane) and quartz microfluidic devices", Analytical and Bioanalytical Chemistry, vol. 401, Issue 7, pp. 2113-2122 (2011).
Bhattacharya S. et al., "Insulator-based dielectrophoretic single particle and single cancer cell trapping", Electrophoresis, vol. 32, Issue 18, pp. 2550-2558 (2011).
Boekema E.J. et al., "Evidence for a trimeric organization of the photosystem I complex from the thermophilic cyanobacterium *Synechococcus* sp.", FEBS Letters, vol. 217, Issue 2, pp. 283-286 (1987).
Weierstall U. et al., "Injector for scattering measurements on fully solvated biospecies", Review of Scientific Instruments. vol. 83, Issue 3, pp. 035108 (2012).
Kissick D.J. et al., "Second-Order Nonlinear Optical Imaging of Chiral Crystals", Annual Review of Analytical Chemistry, vol. 4, pp. 419-437 (2011).
Wampler R.E. et al., "Selective Detection of Protein Crystals by Second Harmonic Microscopy", Journal of the American Chemical Society, vol. 130, Issue 43, pp. 14076-14077 (2008).
Green N.G. et al., "Dielectrophoresis of Submicrometer Latex Spheres. 1. Experimental Results", Journal of Physical Chemistry B, vol. 103, Issue 1, pp. 41-50 (1999).

\* cited by examiner

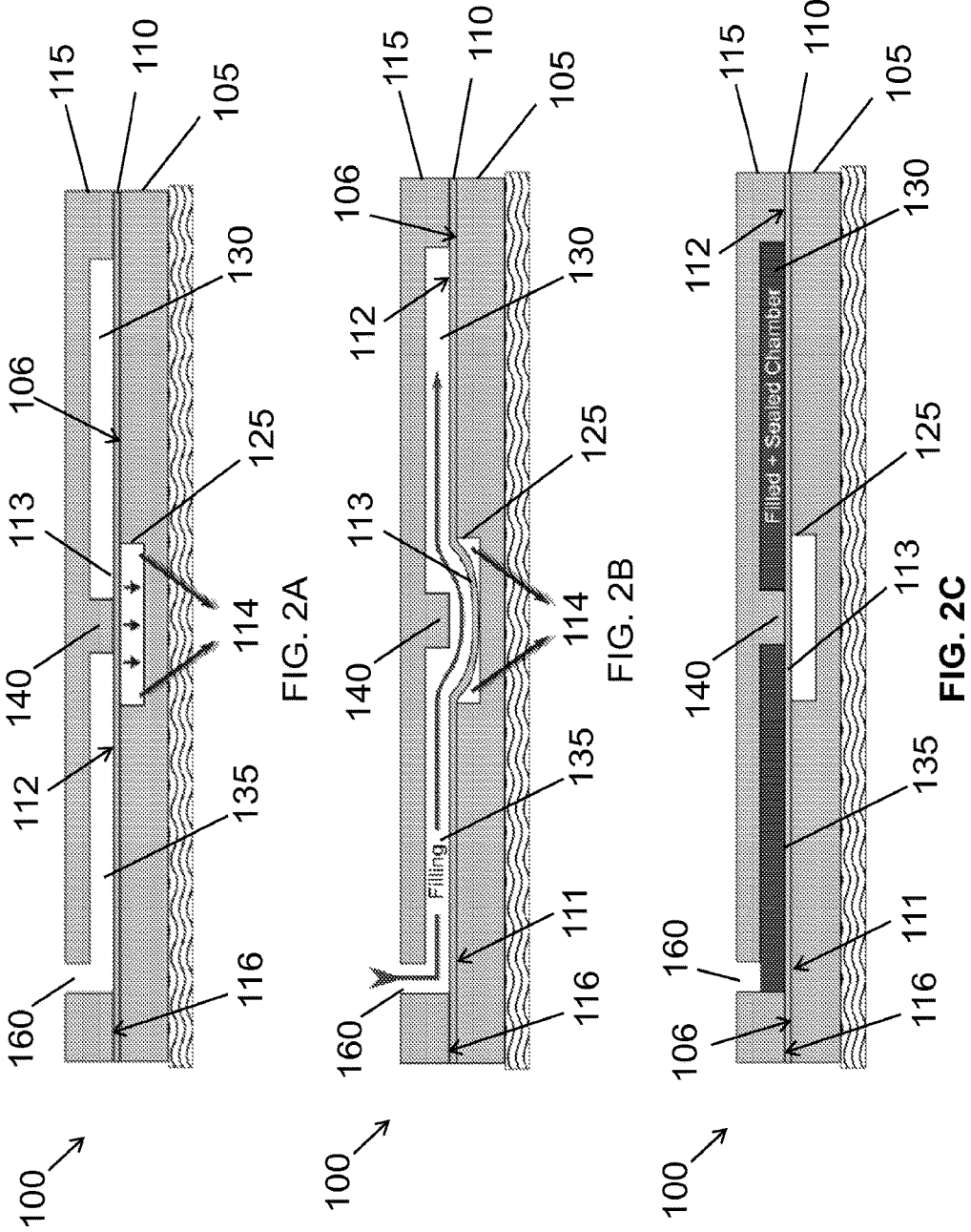

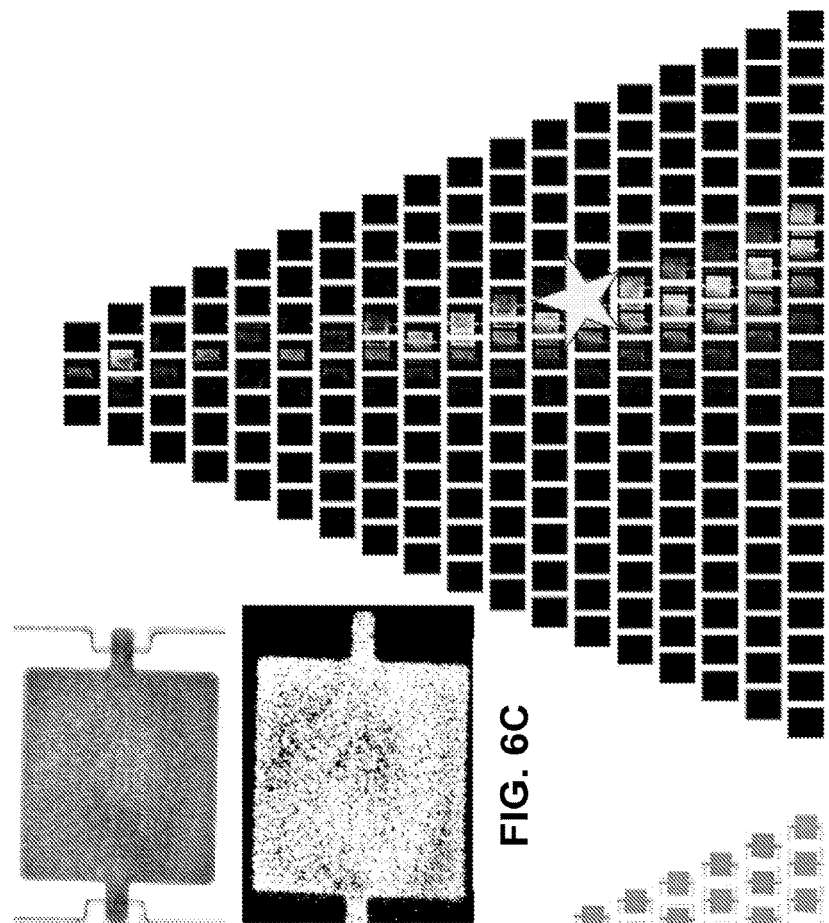
FIG. 6B
FIG. 6C
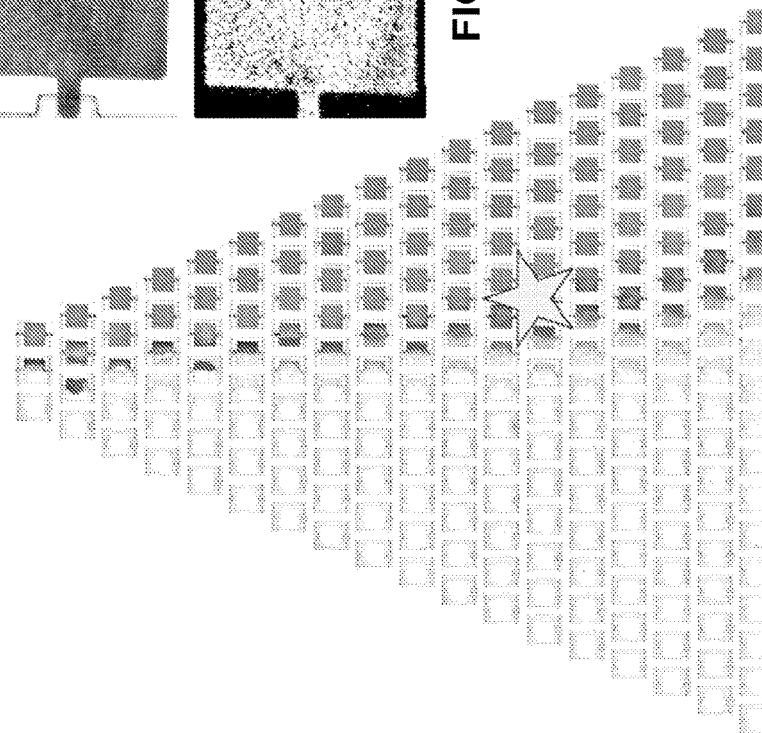
FIG. 6A

METHODS, SYSTEMS AND APPARATUS FOR MICROFLUIDIC CRYSTALLIZATION BASED ON GRADIENT MIXING

CROSS-REFERENCE TO RELATED APPLICATIONS

This application claims the benefit of the filing date of International PCT Application No. PCT/US2015/050616, filed Sep. 17, 2015, that claims priority to U.S. Provisional Application No. 62/051,642 for a Microfluidic Crystallization Array based on Gradient Mixing, filed Sep. 17, 2014, which are hereby incorporated by reference in their entirety.

STATEMENT OF GOVERNMENT FUNDING

This invention was made with government support under R01-GM095583 awarded by the National Institute of Health and under 1231306 awarded by the National Science Foundation BioXFEL Science and Technology Center. The government has certain rights in the invention.

BACKGROUND OF THE INVENTION

Protein crystallography is on the brink of being taken to a new level with the introduction of the X-ray free electron laser, which may be used to solve the structures of complex proteins via serial femtosecond crystallography, for example. Sample crystal characteristics play a role in successful implementation of this new technology, whereby a small, uniform protein crystal size is desired to provide high quality diffraction data. Identifying the conditions of nanocrystal growth and characterizing nanocrystal quality are two limitations in serial femtosecond crystallography. Typically, protein samples may be difficult to retrieve and the sample amount is a pivotal factor in crystallization studies, in particular for large protein complexes such as membrane proteins.

SUMMARY OF THE INVENTION

The present invention provides apparatus, systems and methods for microfluidic crystallization based on gradient mixing are described herein. The invention may beneficially facilitate the study of several hundreds of individual solution combinations in a microfluidic nanowell array for crystal growth, as well as the characterization of the resulting crystals in these nanoliter wells. The microfluidic apparatus may permit parallel high throughput batch crystallization experiments in nanoliter wells arranged in arrays that allow analyte and precipitant solutions to mix, split and recombine as the wells are filled. The array design and integrated valves further permit filling and mixing of analyte solution and precipitant under laminar flow conditions initiated through suction or pressure pumping, for example. The array's arrangement of channels and nanowells, in conjunction with controlled flow rates, may beneficially facilitate the establishment of hundreds of unique concentrations in the plurality of nanowells. Once filled, the nanowells may be advantageously sealed via valves thereby allowing crystallization to occur therein in parallel with each other. Still further, filling of the nanowells may be accomplished using laminar flow that may permit straightforward estimation of concentrations of analyte and precipitant in the nanowell array. Ultimately, numerical simulations based on analyte and precipitant concentration, flow parameters and device geometry, for example, may allow phase diagrams to be constructed to identify nanocrystal growth.

In various embodiments, the microfluidic apparatus may advantageously minimize overall sample consumption and utilize as little as a few microliters of each analyte and precipitant solution for several hundred parallel experiments in the nanowells, rendering the apparatus beneficial for use with precious samples. Still further, filling and mixing of the analyte and precipitant in the nanowells may be accomplished by controlled vacuum suction or pressure pumping, for example, in less than a minute for rapid concentration gradient establishment. Furthermore, hundreds of experiments may be performed in the nanowells of a single apparatus for efficient crystallization screening. Once the nanowells have been filled with the analyte and precipitant solutions, the compartments may be isolated by elastomeric "doormat valve" sealing via a membrane, for example, that may reduce or eliminate interference from both adjacent wells and the environment in order to provide natural, undisturbed crystal growth. Combined, hundreds of trials may be setup rapidly using small sample volumes and conditions may be maintained for days or weeks to crystal growth.

Still further, the apparatus may be fabricated with transparent materials, thereby enabling post-crystal growth imaging within the apparatus using a variety of methods, including, but not limited to, fluorescence microscopy and second order nonlinear imaging of chiral crystals ("SONICC"). Since the mixed analyte and precipitant solutions within the apparatus may be sealed after filling of the wells, the solutions may advantageously remain unexposed to the external environment during imaging thereby avoiding contamination and evaporation issues. As noted above, after imaging, wells where crystals are detected can be located and corresponding analyte and precipitant concentrations may be assigned from the numerical simulations of the mixing phenomena (e.g., solution flow rates and initial concentrations, as well as apparatus geometry). These concentrations in the nanowells may then be plotted as phase diagrams for crystallization of examined analytes. In addition, the invention may permit direct upscaling of crystallization conditions for larger scale experiments in which high crystal throughput and amount are required.

Thus, in a first aspect, the invention provides an apparatus that includes (a) a first layer, (b) a plurality of first channels and a plurality of vacuum chambers both arranged in the first layer, where the plurality of vacuum chambers are each coupled to at least one of the plurality of first channels, (c) a membrane having a first surface and a second surface, where the first surface of the membrane is coupled to the first layer, (d) a second layer coupled to the second surface of the membrane, (e) a plurality of wells and a plurality of second channels both arranged in the second layer, where the plurality of wells are each coupled to at least one of the plurality of second channels and (f) a plurality of barrier walls disposed in the plurality of second channels, where each of the plurality of barrier walls is arranged opposite to one of the plurality of vacuum chambers.

In a second aspect, the invention provides a microfluidic system that includes (a) an apparatus according to the first aspect of the invention, (b) a vacuum source coupled to a vacuum outlet of the apparatus and (c) at least one nozzle, nozzle assembly or injection device coupled to one or more inlets of the apparatus.

In a third aspect, the invention provides a method for microfluidic crystallization based on gradient mixing that includes: (a) advancing an analyte solution into a first inlet of an apparatus according to the first aspect of the invention, (b) advancing a precipitant into a second inlet of the apparatus, (c) advancing the analyte solution and the precipitant through the plurality of second channels and the plurality of wells and (d) mixing the analyte solution and the precipitant at different ratios in the plurality of wells of the apparatus.

The features, functions, and advantages that have been discussed can be achieved independently in various embodiments or may be combined in yet other embodiments further details of which can be seen with reference to the following description and drawings.

BRIEF DESCRIPTION OF THE FIGURES

FIG. 2A is a cross-sectional side view of a second channel in an empty condition, a barrier wall and a vacuum chamber with a membrane in a closed and sealed position, according to one embodiment.

FIG. 2B is a cross-sectional side view of the second channel in a partially-filled condition, a barrier wall and a vacuum chamber with a membrane in an open position, according to the embodiment of FIG. 2A.

FIG. 2C is a cross-sectional side view of a second channel in a filled condition, a barrier wall and a vacuum chamber with a membrane in a closed and sealed position, according to the embodiment of FIG. 2A.

FIG. 6A is a brightfield image of an apparatus with the plurality of wells in a filled condition with a phycocyanin analyte solution and polyethylene glycol ("PEG") (viscous) precipitant after crystallization has occurred, according to one embodiment. Crystals were found in wells with a phycocyanin concentration of approximately 9.5-12.4 mg/ml and a concentration of approximately 5.9-8.5%.

FIG. 6B is a SONICC image of the apparatus of FIG. 6A with the plurality of wells in a filled condition with a phycocyanin analyte solution and PEG precipitant after crystallization has occurred.

FIG. 6C shows a brightfield image of the well overlaid with a star in FIG. 6A (top image) and a SONICC image of the same well overlaid with a star in FIG. 6B (lower image). This well has a concentration of 9.5 mg/ml phycocyanin and 8.5% PEG.

Corresponding parts are marked with the same reference symbols in all figures.

Figure 1:
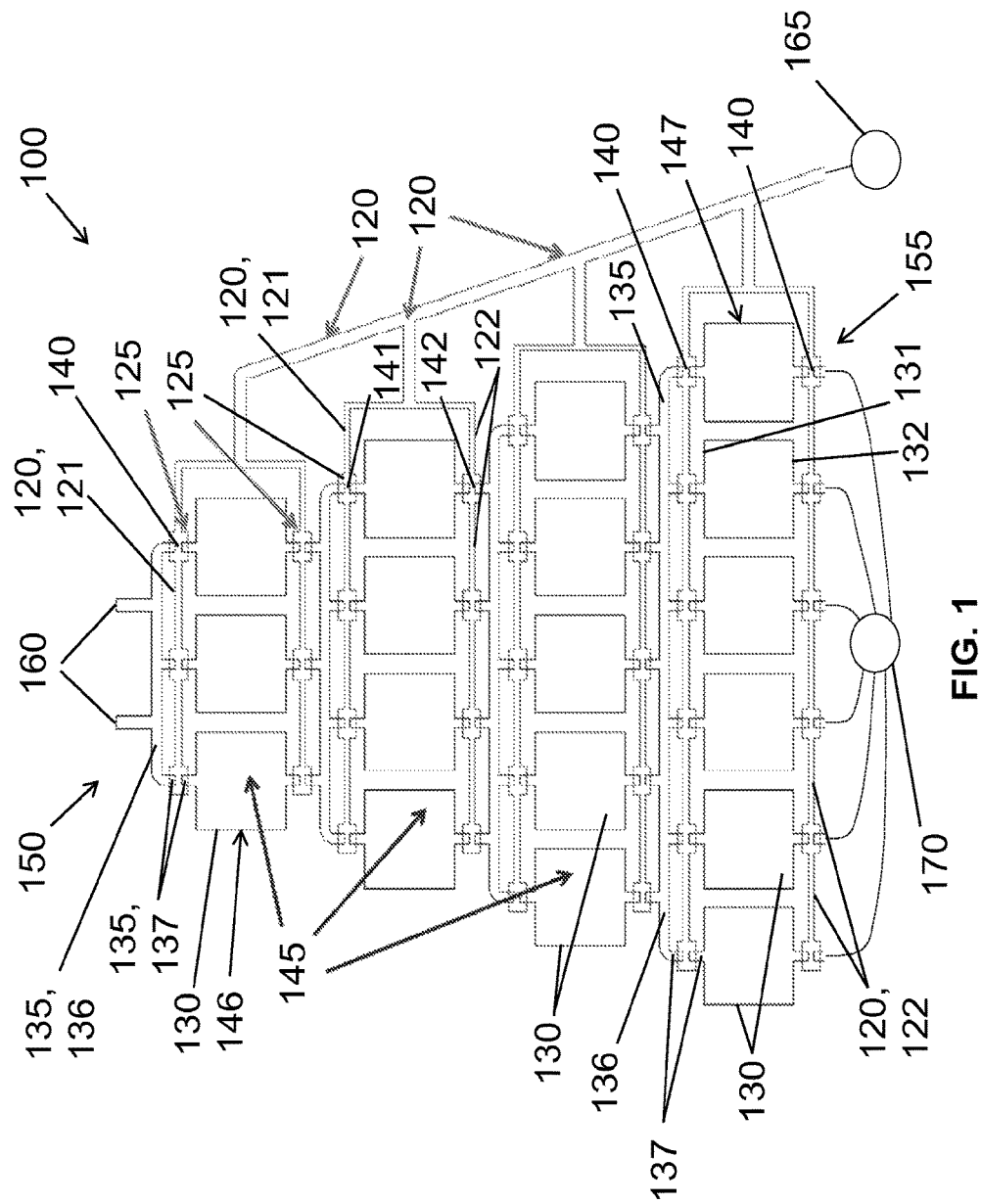
FIG. 1 is a top view of the apparatus, according to one embodiment.
Figure 3A:
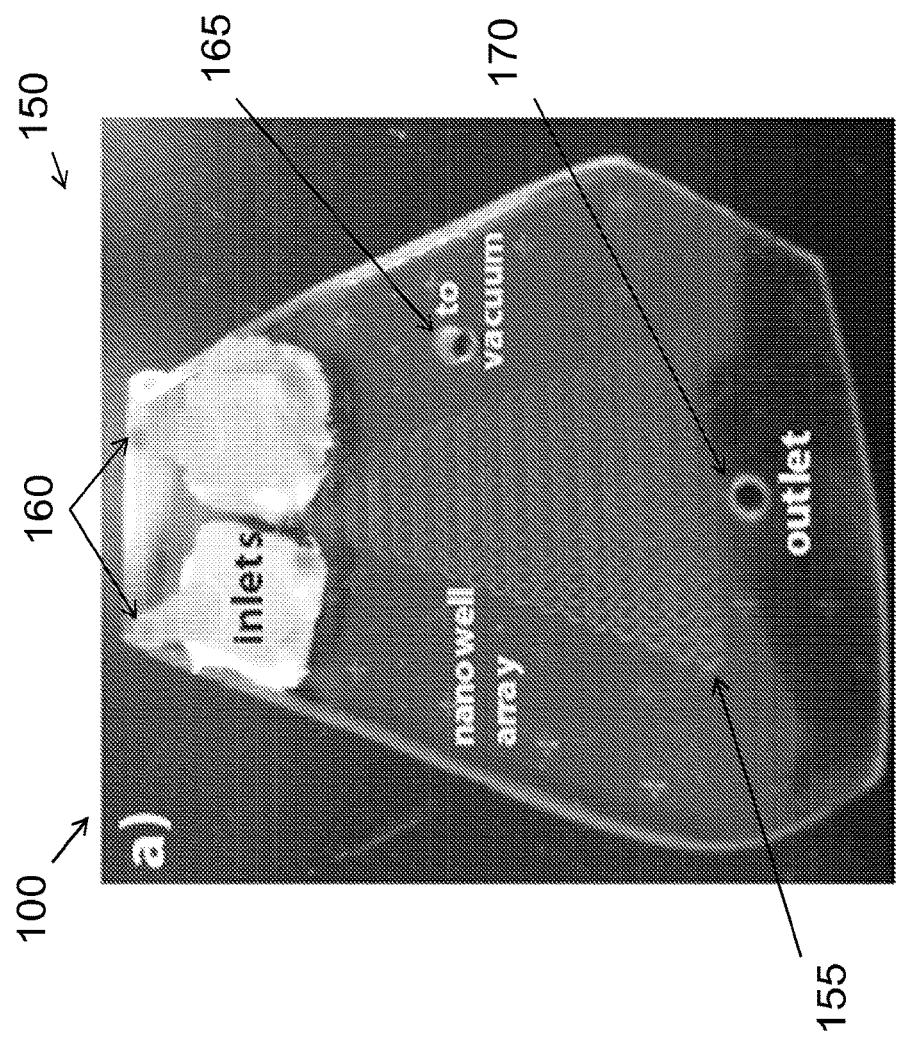
FIG. 3A shows an image of the apparatus in an empty condition, according to one example embodiment.
Figure 3B:
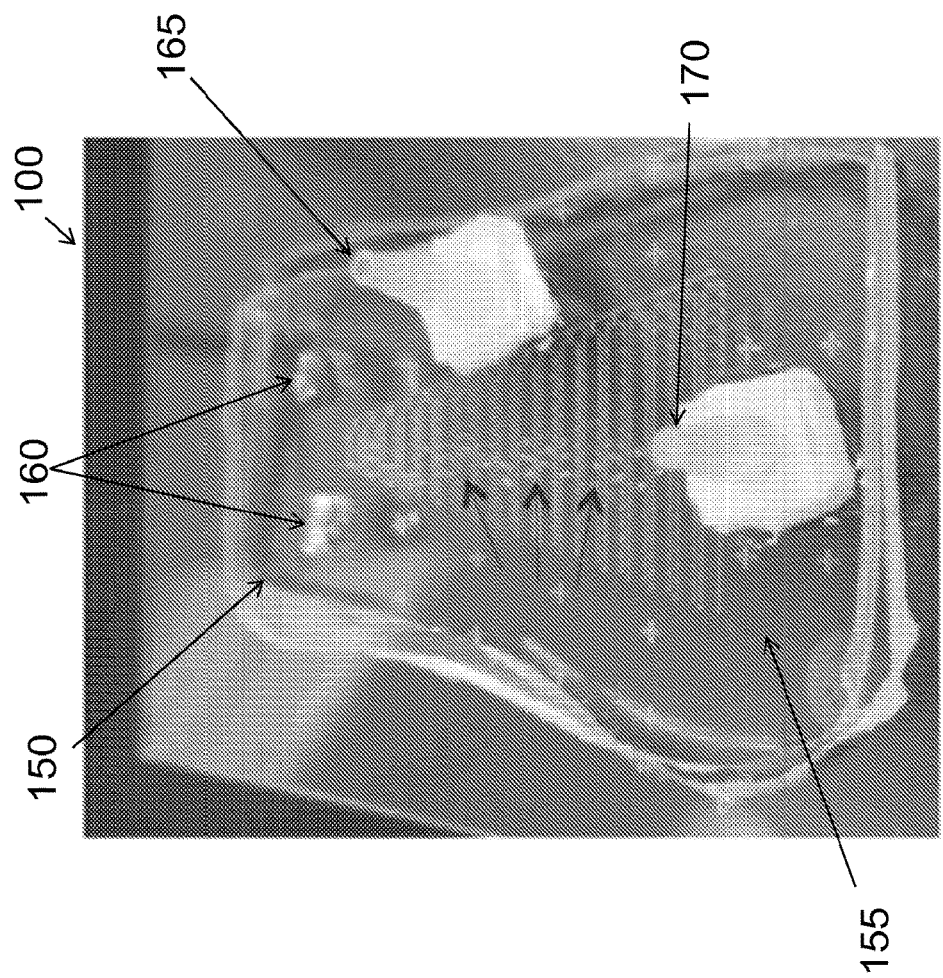
FIG. 3B shows an image of the apparatus of FIG. 3A in a filled condition after crystallization has occurred in the at least one of the plurality of wells.

The drawings are provided for the purpose of illustrating example embodiments, but it is understood that the inventions are not limited to the arrangements and instrumentalities shown in the drawings.

DETAILED DESCRIPTION OF THE INVENTION

As used herein, with respect to measurements and numerical ranges, "about" means +/−5%.

As used herein, the term "analyte solution" may include any suitable particle or analyte including, but not limited to, proteins, such as membrane proteins such as photosystem I (PSI) and pigment protein complexes like photoactive yellow protein (PYP) and phycocyanin, as well as enzymes like lysozymes, and other substances such as nucleic acids, microparticles, nanoparticles, biological cells, viruses, biomolecules, nanocrystals, cancer cells, mitochondria or other cell organelles.

As used herein, the term "precipitant" may include solutions containing salts such as sodium chloride (NaCl), magnesium sulfate ($MgSO_4$) and ammonium sulfate (($NH_4$)$_2SO_4$) or other constituents such as buffering agents, detergents, organic solvents or polymers, for example.

Example microfluidic apparatus, systems and methods for microfluidic crystallization based on gradient mixing are described herein. Any example embodiment or feature described herein is not necessarily to be construed as preferred or advantageous over other embodiments or features. The example embodiments described herein are not meant to be limiting. It will be readily understood that certain aspects of the disclosed apparatus, systems and methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an example embodiment may include elements that are not illustrated in the Figures.

Figure 4A:
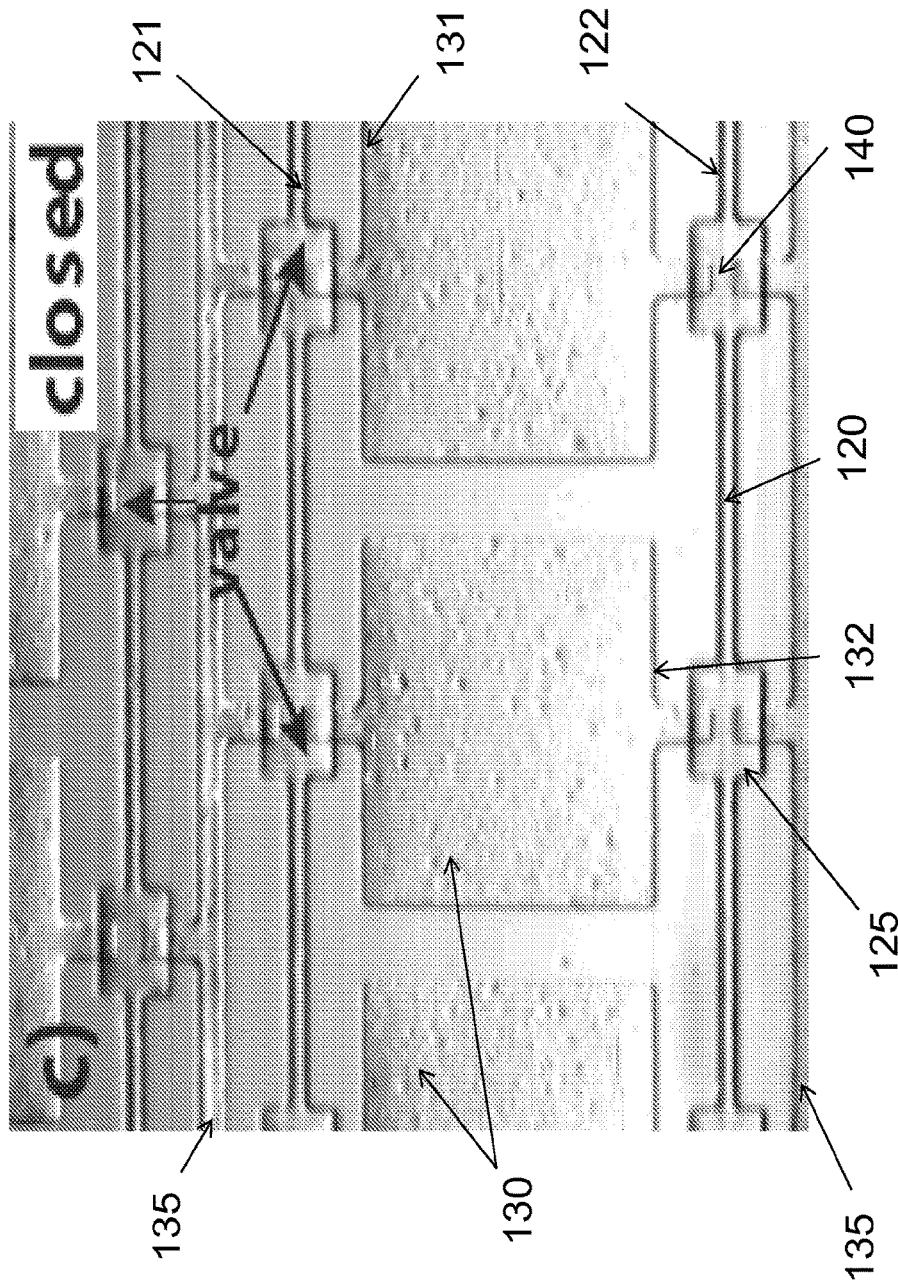
FIG. 4A is an image of a detail view of a plurality of vacuum chambers coupled to a plurality of first channels and a plurality of wells coupled to a plurality of second channels, with a membrane in a closed position above each of the plurality of vacuum chambers, according to one embodiment.
Figure 4B:
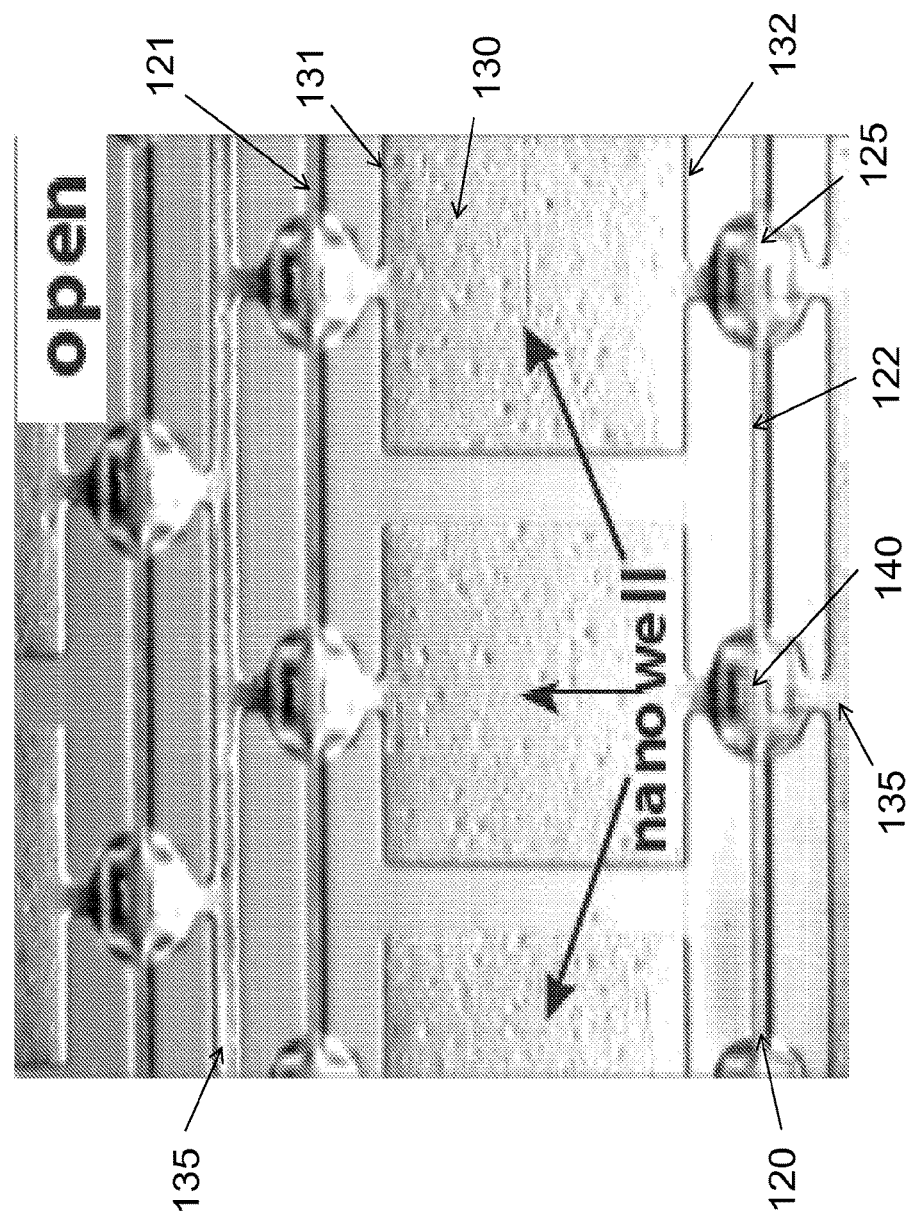
FIG. 4B is an image of a detail view of a plurality of vacuum chambers coupled to a plurality of first channels and a plurality of wells coupled to a plurality of second channels, with a membrane in an open position above each of the plurality of vacuum chambers, according to the embodiment of FIG. 4A.

In a first aspect, as shown in FIGS. 1-4B, the invention provides a microfluidic apparatus 100 for microfluidic crystallization based on gradient mixing. The apparatus 100 includes a first layer 105, a membrane 110 and a second layer 115. In one embodiment, the first layer 105 and the second layer 115 may be made of Polydimethylsiloxane ("PDMS") utilizing photolithography and softlithography, may be made of polymers and photoresists such as injection molding, embossing and/or imprinting, as just some examples, or may be made through microfabrication techniques in glass and silicon or other solid materials. In one embodiment, the second layer may be translucent. In other embodiments, the second layer may be X-Ray transparent or have low X-Ray absorption such as Kapton, cycloolefins or NOA 81 polymers or other polymers. The membrane 110, in turn, may be made of a polymer, elastic or rubber or other material that is flexible and configured to deflect or flex under vacuum 114 and to return to its original position when vacuum is removed. FIG. 4A shows the membrane 110 in a closed, unflexed position, and FIG. 4B shows the membrane in an open, flexed position under vacuum. In one embodiment, the membrane may be non-permeable. The membrane 110 has a first surface 111 and a second surface 112 and is arranged such that the first surface 111 of the membrane 110 is coupled to the first layer 105, and the second layer 115 is coupled to the second surface 112 of the membrane 110.

The first layer 105 has a plurality of first channels 120 and a plurality of vacuum chambers 125 both arranged therein. The plurality of vacuum chambers 125 are each coupled to at least one of the plurality of first channels 120. In one embodiment, the first layer 105 may be configured to withstand vacuum pressure applied to the plurality of first channels 120 and to the plurality of vacuum chambers 125. The apparatus 100 also provides a plurality of wells 130 and a plurality of second channels 135 both arranged in the second layer 115. The wells 130 are each coupled to at least one of the second channels 135. In one embodiment, the second layer 115 may be configured to receive fluid samples in the form of analyte and precipitant solutions in the plurality of second channels 135 and the plurality of wells 130. A plurality of barrier walls 140 are also disposed in the plurality of second channels 135. Each of these barrier walls 140 is arranged opposite to one of the plurality of vacuum chambers 125 such that a portion of the membrane 113 separates the vacuum chamber 125 from a corresponding barrier wall 140. In one embodiment, the first plurality of channels 120 and the plurality of vacuum chambers 125 may be configured to be subject to vacuum and the second plurality of channels 135 and the plurality of wells 130 may be configured to receive one or more fluids.

In one embodiment, shown in FIGS. 2A-2C, the first channels 120 and the vacuum chambers 125 may both be arranged in a top surface 106 of the first layer 105 such that each of the vacuum chambers 125 interface with the portion 113 of the membrane 110 overlying them. In a further embodiment, the wells 130 and the second channels 135 are both arranged in a bottom 116 surface of the second layer 115, such that any fluid in the wells 130 and the second channels 135 may interface with the second surface 112 of the membrane 110. This arrangement may permit vacuum 114 applied to the first channels 120 and the vacuum chambers 125 to act upon the membrane 110, causing the membrane 110 to flex into the vacuum chambers 125. Then fluid advancing in the second channels 135 may pass under the barrier walls 140 extending over the flexed membrane 110 (see FIG. 2B) and into the wells 130. After filling of the wells 130 with fluid is complete and vacuum is removed, the membrane 110 is biased to return to a closed position adjacent the barrier walls 140, as shown in FIG. 2C. Accordingly, the barrier walls 140, the membrane 110 and the vacuum chambers 125 act as self-sealing valves.

In one embodiment, as shown in FIG. 1, the plurality of wells 130 may be arranged in a plurality of rows 145 between a first end 150 and a second end 155 of the second layer 115 such that a first row 146 of the plurality of rows of wells 145 comprises at least two wells 130 and each subsequent row comprises at least one more well 130 than a preceding row. In one embodiment, the first row 146 of the plurality of rows of wells 145 may have three wells 130, as shown in FIG. 1. This arrangement may beneficially promote mixing, splitting and remixing of an analyte solution and a precipitant solution as the fluid moves between wells 130 from the first end 150 to the second 155 of the apparatus 100.

In another embodiment, the apparatus may provide at least two inlets 160 each coupled to one of the plurality of second channels 135 arranged at the first end 150 of the apparatus 100. In operation, an analyte solution may be advanced into one inlet 160 and a precipitant solution may be advanced into another inlet 160 and may mix together within the second channels 135 and wells 130. In a further embodiment, the apparatus 100 may include a first outlet 165 coupled to at least one of the first channels 120. This first outlet 165 may be configured to be coupled to a vacuum source that may cause the membrane 110 to deflect during filling of the second channels 135 and wells 130 thereby allowing solution to pass underneath barrier walls 140, as shown in FIG. 2B. In yet another embodiment, a second outlet 170 may be coupled to at least one of the second channels 135 that is arranged at the second end of the apparatus 100. This second outlet 170 may be coupled to a vacuum source or may alternatively be coupled to a receptacle with ambient conditions to receive any overflow solution during filling of the second channels 135 and wells 130.

In a further embodiment, the first channels 120 may be arranged as rows in the form of a plurality of input channels 121 and a plurality of output channels 122, as shown in FIG. 1. The input channels 121 may each be disposed at a first end 131 of each of the plurality of rows of wells 145 and the output channels 122 may each be disposed at a second end 132 of each of the plurality of rows of wells such that a vacuum chamber 125 may be arranged on either end of each well 130 to facilitate sealing of each well 130 after filling with fluid. Accordingly, in another embodiment, each of the barrier walls 140 may include a plurality of input barrier walls 141 arranged adjacent to a first end 131 of one of the plurality of wells 130 and a plurality of output barrier walls 142 arranged adjacent to a second end 132 of one of the plurality of wells 130. Each of these barrier walls 140 are arranged over a respective vacuum chamber 125. In one embodiment, the second channels 135 may be arranged in a plurality of rows 136 having extensions 137 arranged over each of the vacuum chambers 125. In addition, the input channels 121 may each be arranged between one of the second channels 135 and one of the rows of wells 145.

In a second aspect, the invention provides a microfluidic system for microfluidic crystallization based on gradient mixing. The system includes an apparatus 100 according to the first aspect of the invention. The system also provides a vacuum source coupled to a first outlet 165 of the apparatus 100. And the system includes at least one nozzle, nozzle assembly or injection device coupled to one or more inlets 160 of the apparatus 100. Example nozzles are described in U.S. Pat. No. 8,272,576, entitled Gas Dynamic Virtual Nozzle for Generation of Microscopic Droplet Streams, in U.S. patent application Ser. No. 13/680,255, filed Nov. 19, 2012, entitled Apparatus and Methods for a Gas Dynamic Virtual Nozzle, in U.S. Pat. No. 7,341,211, entitled Device for the Production of Capillary Jets and Micro- and Nanometric Particles or in U.S. Published Application No. 2010/0163116, published Jul. 1, 2010, entitled Microfluidic Nozzle Formation and Process Flow, the disclosures of which are herein incorporated by reference. The foregoing example nozzles are not intended to be limiting, as the microfluidic apparatus may be used in conjunction with a wide variety of microfluidic nozzles capable of producing a jet, a stream, or fluid flow in general.

In one embodiment, the system may further include a device configured to separate and sort particles based on dielectrophoresis ("DEP") coupled to at least one inlet 160 of the apparatus 100. An example, DEP sorting device is described in U.S. patent application Ser. No. 14/041,712, filed Sep. 30, 2013, entitled Methods, Systems and Apparatus for Size-Based Particle Separation. The foregoing example sorting device is not intended to be limiting, as the microfluidic apparatus 100 may be used with a wide variety of sorting devices capable of sorting micro- and nanoparticles, crystals and cells. Alternatively, in one embodiment, the microfluidic DEP sorting device and the nozzle may be arranged such that the nozzle is in fluid communication with any outlet reservoir of the DEP sorting device such that the nozzle receives a portion of the sorted bulk solution in operation.

In a third aspect of the invention, a method is provided for microfluidic crystallization based on gradient mixing that includes the step of advancing an analyte solution into a first inlet 160 of an apparatus 100 or system according to the first or second aspects of the invention, respectively. At the same time, a precipitant solution is advanced into a second inlet 160 of the apparatus 100. Then the analyte solution and the precipitant solution are advanced through the plurality of second channels 135 and the plurality of wells 130. Advancement of the solutions may be achieved either by applying pressure to the first and second inlets 160 of the apparatus 100 or by applying vacuum to a second outlet 170 of the apparatus 100. In one embodiment, a total combined volume of the analyte solution and precipitant solution advanced into the plurality of second channels and the plurality of wells may be 10 µL or less. In another embodiment, the flow rate of the analyte solution and the precipitant solution may be about 10 mm/s. The analyte solution and the precipitant solution are next mixed at different ratios in the plurality of wells 130 of the apparatus 100.

In one embodiment, the method may include applying a vacuum pressure to the plurality of first channels 120 via a first outlet 170 (see, e.g., FIG. 2A), thereby deflecting the membrane 110 in each of the plurality of vacuum chambers 125 (e.g., FIG. 2B). Next, the analyte solution and the precipitant solution may be advanced through the plurality of second channels 135 and past the plurality of barrier walls 140 disposed opposite to the plurality of vacuum chambers 125. In another embodiment, the vacuum pressure may be removed from the plurality of first channels 120 thereby permitting the membrane 110 to return to a closed position and sealing the plurality of wells 130 (e.g., FIG. 2C).

In another embodiment, the method may provide tuning crystallization conditions. In one embodiment tuning of crystallization conditions may involve adjusting one or more of (i) a number of inlets 160, (ii) a concentration of one or both of the precipitant solution and the analyte solution, (iii) a flow rate of one or both of the precipitant solution and the analyte solution and (iv) and a geometry of the plurality of wells and the plurality of second channels.

A further embodiment may provide that, after the wells 130 have been filled, the mixed analyte solution and precipitant solution may be permitted to crystallize in one or more of the plurality of wells over a period of time. In various embodiments, the period of time may be at least about 24 hours, still further crystallization may occur over a period of days or weeks.

Figures 5A, 5B, 5C:
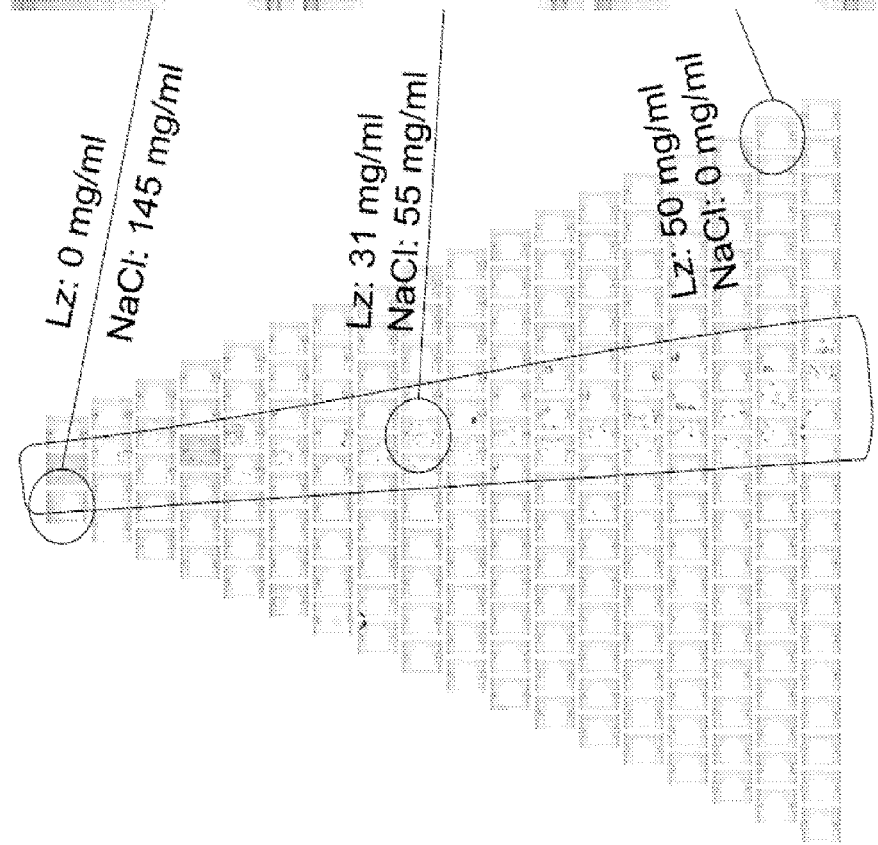
FIG. 5A is a brightfield image of an apparatus with the plurality of wells in a filled condition with a Lysozyme analyte solution and NaCl precipitant after crystallization has occurred, according to one embodiment. Crystals were found in wells with a lysozyme concentration of approximately 28-35 mg/ml and a concentration of approximately 44-63 mg/ml.
FIG. 5B shows three brightfield images of (i) a well in a first row of the apparatus shown in FIG. 5A having a lysozyme concentration of 0 mg/ml and a NaCl concentration of 145 mg/ml, (ii) a well in a ninth row of the apparatus and crystals therein shown in FIG. 5A having a lysozyme concentration of 31 mg/ml and a NaCl concentration of 55 mg/ml and (iii) a well in a seventeenth row of the apparatus shown in FIG. 5A having a lysozyme concentration of 50 mg/ml and a NaCl concentration of 0 mg/ml.
FIG. 5C shows three UV images of (i) the well in a first row of the apparatus shown in FIGS. 5A and 5B having a lysozyme concentration of 0 mg/ml and a NaCl concentration of 145 mg/ml, (ii) a well in a ninth row of the apparatus and crystals therein shown in FIGS. 5A and 5B having a lysozyme concentration of 31 mg/ml and a NaCl concentration of 55 mg/ml and (iii) a well in a seventeenth row of the apparatus shown in FIGS. 5A and 5B having a lysozyme concentration of 50 mg/ml and a NaCl concentration of 0 mg/ml.

Once crystallization occurs, crystals may be detected in at least one of the plurality of wells via microscopy, fluorescence, 2-photon-fluorescence or second order nonlinear imaging of chiral crystals. The invention beneficially may permit these observations within the apparatus itself without retrieval of the crystals from the wells. One example appears in FIG. 5A that shows a brightfield image an apparatus with the plurality of wells in a filled condition with a Lysozyme analyte solution and a NaCl precipitant solution after crystallization has occurred. Crystals were found in wells with a lysozyme concentration of approximately 28-35 mg/ml and a concentration of approximately 44-63 mg/ml. FIG. 5B shows a brightfield image and 5C shows a UV image of the following: (i) a well in a first row of the apparatus has a lysozyme concentration of 0 mg/ml and a NaCl concentration of 145 mg/ml, (ii) a well in a ninth row of the apparatus has crystals therein and has a lysozyme concentration of 31 mg/ml and a NaCl concentration of 55 mg/ml and (iii) a well in a seventeenth row of the apparatus has a lysozyme concentration of 50 mg/ml and a NaCl concentration of 0 mg/ml. This illustrates how a gradient forms from the first end of the apparatus to the second end of the apparatus. Another example is shown in FIGS. 6A-6C. Specifically, FIG. 6A is a brightfield image and FIG. 6B is a SONICC image of an apparatus in a filled condition with a Phycocyanin analyte solution and polyethylene glycol ("PEG") (viscous) precipitant after crystallization has occurred, according to one embodiment. Crystals were found in wells with a phycocyanin concentration of approximately 9.5-12.4 mg/ml and a concentration of approximately 5.9-8.5%. FIG. 5C shows the starred well of FIGS. 5A and 5B; a well that has a concentration of 9.5 mg/ml phycocyanin and 8.5% PEG.

In one embodiment, diffraction analysis of crystals may be performed within at least one of the plurality of wells via a free electron laser.

In still another embodiment, after detecting crystals in at least one of the wells, a numerical simulation of mixing phenomena of the analyte solution and the precipitant solution may be performed. Then a concentration of the analyte solution and a concentration of the precipitant solution may be determined for one or more of the plurality of wells.

In one embodiment, the analyte solution and the precipitant solution may advance with laminar flow through the plurality of second channels and the plurality of wells during filling. Laminar flow, as opposed to turbulent flow, may improve reliability of the numerical simulation for purposes of mapping solution concentrations.

The method according to the third aspect of the invention may be carried out using the microfluidic apparatus or system according to any of the first and second aspects of the invention. Note further that any of the foregoing embodiments of any aspect may be combined together to practice the claimed invention.

It is intended that the foregoing detailed description be regarded as illustrative rather than limiting and that it is understood that the following claims, including all equivalents, are intended to define the scope of the invention. The claims should not be read as limited to the described order or elements unless stated to that effect. Therefore, all embodiments that come within the scope and spirit of the following claims and equivalents thereto are claimed as the invention.

The invention claimed is:

1. An apparatus, comprising:
    a first layer;
    a plurality of first channels and a plurality of vacuum chambers both arranged in the first layer, wherein the plurality of vacuum chambers are each coupled to at least one of the plurality of first channels;
    a membrane biased to a closed position, the membrane having a first surface and a second surface, wherein the first surface of the membrane is coupled to the first layer;
    a second layer coupled to the second surface of the membrane;
    a plurality of wells and a plurality of second channels both arranged in the second layer, wherein the plurality of wells are each coupled to at least one of the plurality of second channels;
    a plurality of barrier walls disposed in the plurality of second channels, wherein each of the plurality of barrier walls is arranged opposite to one of the plurality of vacuum chambers.

2. The apparatus of claim 1, wherein the plurality of wells are arranged in a plurality of rows between a first end and a second end of the second layer such that a first row of the plurality of rows of wells comprises at least two wells and each subsequent row comprises at least one more well than a preceding row.

3. The apparatus of claim 2, wherein the first row of the plurality of rows of wells has three wells.

4. The apparatus of claim 2, wherein the plurality of first channels comprise a plurality of input channels and a plurality of output channels each arranged as rows, wherein the plurality of input channels are each disposed at a first end of each of the plurality of rows of wells and the plurality of output channels are each disposed at a second end of each of the plurality of rows of wells.

5. The apparatus of claim 2, wherein the plurality of second channels are arranged in a plurality of rows having extensions arranged over each of the plurality of vacuum chambers and wherein the plurality of input channels are each arranged between one of the plurality of second channels and one of the plurality of rows of wells.

6. The apparatus of claim 2, further comprising:
    at least two inlets each coupled to one of the plurality of second channels arranged at the first end.

7. The apparatus of claim 1, further comprising:
    a first outlet coupled to at least one of the plurality of first channels.

8. The apparatus of claim 2, further comprising:
    a second outlet coupled to at least one of the plurality of second channels arranged at the second end of the apparatus.

9. The apparatus of claim 1, wherein each of the plurality of barrier walls comprise a plurality of input barrier walls and a plurality of output barrier walls, wherein each of the plurality of input barrier walls is arranged adjacent to a first end of one of the plurality of wells and each of the plurality of output barrier walls is arranged adjacent to a second end of one of the plurality of wells.

10. The apparatus of claim 1, wherein the membrane is flexible and configured to deflect when subjected to vacuum pressure.

11. The apparatus of claim 1, wherein the membrane is non-permeable.

12. The apparatus of claim 1, wherein the plurality of first channels and the plurality of vacuum chambers are both arranged in a top surface of the first layer and the plurality of wells and the plurality of second channels are both arranged in a bottom surface of the second layer.

13. The apparatus of claim 1, wherein the first plurality of channels and the plurality of vacuum chambers are configured to be subject to vacuum and the second plurality of channels and the plurality of wells are configured to receive one or more fluids.

14. The apparatus of claim 1, wherein the second layer is translucent, is X-Ray transparent or has low X-Ray absorption.

15. The apparatus of claim 1, wherein the first layer is configured withstand vacuum pressure applied to the plurality of first channels and to the plurality of vacuum chambers and wherein the second layer is configured to receive fluid samples in the form of analyte and precipitant solutions in the plurality of wells and in the plurality of second channels.

16. A microfluidic system, comprising:
    an apparatus according to claim 1;
    a vacuum source coupled to a first outlet of the apparatus; and
    at least one nozzle, nozzle assembly or injection device coupled to one or more inlets of the apparatus.

17. The microfluidic system of claim 16, further comprising:
    a device configured to separate and sort particles based on dielectrophoresis coupled to at least one inlet of the apparatus.

18. A method, comprising:
    advancing an analyte solution into a first inlet of an apparatus according to claim 1;
    advancing a precipitant solution into a second inlet of the apparatus;
    advancing the analyte solution and the precipitant through the plurality of second channels and the plurality of wells; and
    mixing the analyte solution and the precipitant solution at different ratios in different wells within the plurality of wells of the apparatus.

19. The method of claim 18, further comprising:
    applying a vacuum pressure to the plurality of first channels via a first outlet and thereby deflecting the membrane in each of the plurality of vacuum chambers; and
    advancing the analyte solution and the precipitant solution through the plurality of second channels and past the plurality of barrier walls disposed opposite to the plurality of vacuum chambers.

20. The method of claim 18, wherein advancing the analyte solution and the precipitant solution through the plurality of second channels and the plurality of wells comprises either applying pressure to the first inlet and the second inlet of the apparatus or applying vacuum to a second outlet of the apparatus.

* * * * *